United States Patent [19]

Huth et al.

[11] Patent Number: 5,049,383

[45] Date of Patent: Sep. 17, 1991

[54] AQUEOUS BIOCIDAL CATIONIC DISPERSIONS OF POLYMERS AND THEIR USE AS FUNGICIDAL, BACTERICIDAL AND ALGICIDAL TREATMENT AGENTS

[75] Inventors: Hans-Ullrich Huth, Langen; Helmut Braun, Kriftel; Franz König, Frankfurt am Main, all of Fed. Rep. of Germany

[73] Assignee: Hoechst AG, Fed. Rep. of Germany

[21] Appl. No.: 458,966

[22] Filed: Dec. 29, 1989

Related U.S. Application Data

[63] Continuation of Ser. No. 177,697, Apr. 5, 1987, abandoned.

[30] Foreign Application Priority Data

Apr. 7, 1987 [DE] Fed. Rep. of Germany ....... 3711680

[51] Int. Cl.$^5$ ..................... A01N 25/04; A01N 33/12; A01N 25/02; B05D 3/02
[52] U.S. Cl. .................................. 424/405; 424/78; 424/81; 427/393; 514/642; 514/643; 514/937
[58] Field of Search .................. 424/78, 405; 514/642, 514/643, 937; 260/501.13; 427/393, 393.6

[56] References Cited

U.S. PATENT DOCUMENTS

| | | | |
|---|---|---|---|
| 3,988,294 | 10/1976 | Hill | 514/596 |
| 4,256,804 | 3/1981 | Jasperson | 428/332 |
| 4,304,703 | 12/1981 | Das | 525/260 |
| 4,675,374 | 6/1987 | Mochizuki et al. | 528/119 |
| 4,839,373 | 6/1989 | Ito et al. | 514/367 |

FOREIGN PATENT DOCUMENTS 1546236 10/1969 Fed. Rep. of Germany.

*Primary Examiner*—Thurman K. Page
*Assistant Examiner*—Carlos Azpuru
*Attorney, Agent, or Firm*—Bierman and Muserlian

[57] ABSTRACT

Use of fine-particled biocidal aqueous cationic dispersions of polymers as biocidal treatment agents for substrates at risk from microbes, preferably for fungicidal, bactericidal and/or algicidal treatments. The dispersions of polymers used are biocidal cationic dispersions of polymers which can be obtained from suitable monomers by emulsion polymerization and which contain biocidal cationically surfactant quaternary organic ammonium compounds, preferably tetra-substituted ammonium compounds of the formula (I) and/or alkyl- or alkenylpyridinium compounds of the formula (II), in particular in an amount of 0.1 to 20% by weight, based on the disperse polymer. The average particle diameter of the polymer particles in the biocidal cationic dispersions of polymers is preferably 0.02 to 0.5 $\mu$m at a cationic activity of 1.5 to 600 $\mu$mol per g of solid, measured at pH 7, and the solids content of the dispersions is preferably 3 to 40% by weight. The biocidal cationic dispersions are preferably used as treatment agents for the preservation of wood, for emulsion paint films and for polymer plasters or synthetic resin plasters, it being possible for the biocidal treatments which can be achieved to display surprising long-term biological actions.

10 Claims, No Drawings

AQUEOUS BIOCIDAL CATIONIC DISPERSIONS OF POLYMERS AND THEIR USE AS FUNGICIDAL, BACTERICIDAL AND ALGICIDAL TREATMENT AGENTS

PRIOR APPLICATION

This application is a continuation of U.S. patent application Ser. No. 177,697, filed Apr. 5, 1988, now abandoned.

The invention relates to aqueous biocidal cationic dispersions of polymers and their use as biocidal treatment agents, preferably for wood preservation, for emulsion paints and for synthetic resin plasters.

Many types of wood, including numerous native types, have only a low natural durability. Under the action of moisture in particular, for example when used outside closed rooms or within humid rooms with little ventilation, the risk of population and destruction of wood left in its natural form by fungi and microorganisms is high. There has therefore been no lack of attempts to reduce the susceptibility of commercial timber. Solutions or mixtures of polymeric binders with fungicidal compounds, often phenol derivatives (for example Preventol), polyhalogenohydrocarbons (for example HCH or PCP) or tin compounds (tributyltin oxide) in combination with organic solvents thus have been and are often still being used as wood preservatives. The disadvantages of these systems are, amongst other things, the considerable toxicological objections in respect of the active substances, the frequent combustibility of the agents and their pungent smell, which excludes or limits use, for example in living space. The high cost of the solvents and the adverse effects on human health and the environment when they are released into the atmosphere are further disadvantages. In addition, the effectiveness of the wood preservatives known to date often decreases rapidly, since the biocidal active substances, in spite of their frequent water-insolubility, are leached out relatively rapidly, for example under weathering in the open, and can then contaminate the environment as a result of their usually inadequate biological degradability.

Similar difficulties exist in preserving emulsion paints and synthetic resin plasters with the usual biocidal active substances. In contrast to the preservation of wood, however, in the two latter cases it is a matter of preservation of the coating itself, since constituents of the binder and the polymeric material itself, because of its composition, are used directly as a basis for nutrition or at least as a habitat by many harmful organisms, such as molds and algae, especially where the living conditions for microorganisms are ideal (high atmospheric humidity, heat and, if appropriate, sufficient light). Here also, previous preservatives have not offered sufficient protection, especially in humid interior rooms (bathrooms).

The use of anionic dispersions of polymers as binders for paints and plasters and for glazing wood is already known. Products of this type do not pollute the environment and also meet the requirement of a wood coating very well in the esthetic respect. A disadvantage is that by themselves they cannot provide the wood with sufficient protection from rot and attack by fungi. However, an effective addition of the abovementioned free active substances, such as phenol compounds, polyhalogenohydrocarbons and tin compounds, with their disadvantages already mentioned, is possible only with difficulty. For example, they cannot be recommended for internal applications, in particular for toxicological reasons. In spite of their water-insolubility, they moreover also guarantee only short-term protection when subjected to leaching.

The preparation and use of cationic dispersions of polymers is also already known. Thus, DE-AS 1,053,783 describes for the first time the preparation of quaternary, ethylenically unsaturated ammonium compounds which are capable of polymerization and their use as monomers in emulsion, solution or block polymerization. These salt-like functional monomers can be copolymerized, for example, with vinyl esters, styrene, acrylic esters, olefins and also other unsaturated compounds. If the polymerization is carried out in emulsion, surface-active compounds from the group comprising nonionic emulsifiers, such as fatty acid polyglycol esters, fatty alcohol polyglycol ethers and alkylphenol polyglycol ethers, or cationic surfactants, such as salts of fatty amines or quaternary alkylammonium compounds, can be used. The products obtained are described as auxiliaries for the textile, leather and paper industry and for the production of films, fibers, adhesives and lacquers. On the other hand, nothing is said or mentioned of properties in respect of a use in wood preservatives.

A process for the production of sized papers by treatment of fiber materials or webs of paper with aqueous cationic dispersions is known from DE-PS 1,546,236. The disperse polymers consist to the extent of 20-60% by weight of styrene and/or acrylonitrile, to the extent of 20-60% by weight of (meth)acrylic esters and to the extent of 5-50% by weight of ethylenically unsaturated compounds with a quaternary nitrogen atom. However, the publication contains no information on a use of the cationic dispersions of polymers other than those in the paper sector.

The use of cationic emulsifiers, such as, for example, amines, amine oxides or quaternary alkylammonium compounds, as stabilizing components in the preparation of dispersions of polymers is furthermore also known. As well as their effectiveness as a stabilizer in emulsion polymerization, some quaternary ammonium compounds (for example benzalkonium chloride) generally also have per se germicidal properties, for example against yeasts, bacteria and molds. However, this general action is not sufficient for permanent protection of wood or disperse polymers or plasters, for example from blue fungi and molds and from algae, when such products are employed as emulsifiers in the usual amounts, so that the customary cationic dispersions have not hitherto found application as an effective protection of substrates against attack by microorganisms.

Addition of cationic emulsifiers to the known anionic dispersions is also not possible without reservation, because anionic dispersions, inter alia for reasons of the stability of the dispersion, generally do not tolerate additions of cationic emulsifiers, since these cause coagulation of anionic dispersions.

The present invention was therefore based on the object of making available biocidal aqueous dispersions of polymers which, while overcoming the disadvantages described above for known dispersions, can meet the requirements for biocidal aqueous dispersions of polymers for treating wood both in the esthetic and in the fungicidal, bactericidal and algicidal respect and are easy to use and do not pollute the environment. It should moreover also be possible to use the dispersions to prevent microbial attack on emulsion paint films and on synthetic resin plasters or polymer plasters.

It has now been found, surprisingly, that the above-mentioned difficulties can be overcome if fine-particled aqueous cationic dispersions of polymers to which biocidal cationically surfactant quaternary organic ammonium compounds have been added during or after preparation are used.

The invention thus relates to the use of fine-particled aqueous cationic dispersions of polymers as biocidal treatment agents for substrates at risk from microbes, preferably for wood preservation, for coats of emulsion paint, for polymer plasters and for synthetic resin plasters, and/or for the preparation of wood preservatives, emulsion paints, polymer plasters and synthetic resin plasters, wherein the dispersions contain biocidal cationically surfactant quaternary organic ammonium compounds, preferably compounds of the formula (I) and/or (II)

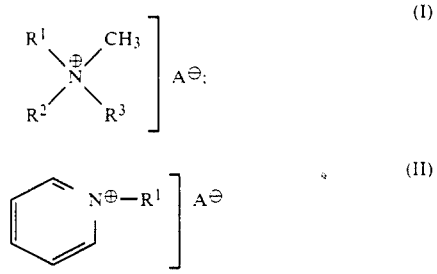

in which
$R^1 = (C_8-C_{18})$-alkyl or -alkenyl, preferably -alkyl,
$R^2 = (C_8-C_{18})$-alkyl or -alkenyl, preferably -alkyl, aryl or $(C_7-C_{18})$-aralkyl, in which the aromatic rings can additionally be substituted, preferably by chlorine and/or bromine,
$R^3 = (C_1-C_4)$-alkyl, preferably methyl, or the radical $-(CH_2-CHR^4O)_n-R^5$, in which n denotes a number from 1 to 20 and $R^4$ and $R^5$, which can be identical or different, denote H and/or $(C_1-C_4)$-alkyl, $R^4$ preferably denoting H or methyl and $R^5$ preferably denoting H, and
A = an anion of an organic or inorganic acid.

Possible anions A are, for example, chloride, bromide, acetate, propionate, benzoate or 1 equivalent of sulfate.

The biocidal cationic dispersions according to the invention preferably contain 0.1 to 20% by weight, in particular 0.1 to 10% by weight and particularly preferably 0.1 to 3% by weight, based on the disperse polymer, of one or more compounds of the formula (I) and/or (II), the particles of the disperse polymer or of the solids content of the dispersion having an average particle diameter of preferably 0.02 to 0.5 μm, in particular 0.05 to 0.2 μm and particularly preferably 0.08 to 0.15 μm.

The radicals $R^1$ and $R^2$ in formula (I) can be identical or different. Those surfactant compounds of the formula (I) in which at least one of the radicals $R^1$ and $R^2$ stands for $(C_{10}-C_{12})$-alkyl or both radicals $R^1$ and $R^2$ denote $(C_{10}-C_{12})$-alkyl exhibit a particular biocidal activity.

Active compounds of the formula (I) and (II) are, for example, octyl-trimethylammonium bromide, decyl-trimethyl-ammonium chloride, didecyl-dimethylammonium chloride, dedecyl-methylhydroxyethylammonium propionate, lauryl-trimethylammonium chloride, lauryl-pyridinium chloride, hexadecyl-trimethylammonium chloride, stearyl-trimethylammonium chloride and stearyl-dimethylbenzylammonium chloride.

In particular, didecyl-dimethylammonium compounds show, in cationic dispersions to which they have been added either already during the emulsion polymerization or subsequently to the finished cationic dispersion, are particularly effective as wood preservatives against attack by fungi which destroy wood and against algae, and above all the low leachability of the agent, which is important for long-lasting protection, is to be emphasized.

By addition of biocidal cationically surfactant compounds, preferably compounds of the formula (I) and/or (II), to cationic dispersions of polymers, the overall cationic activity of the latter is increased. Thus, in the biocidal dispersions to be used according to the invention, the cationic activity content from the biocidal cationically surfactant compounds, for example of the formula (I) and/or (II), is in general 5 to 95%, preferably 15 to 50%, based on the total cationic activity of the dispersions which are ready for use according to the invention.

The aqueous fine-particled cationic starting dispersions on which the biocidal cationic dispersions of polymers, according to the invention, are based are preferably prepared by customary emulsion polymerization or emulsion copolymerization. Biocidal cationically surfactant compounds, preferably compounds of the formula (I) and/or (II), can thereby be added in various ways, and in particular:

1. The biocidal cationically surfactant compounds, preferably compounds of the formula (I) and/or (II), are used as emulsifiers in the emulsion polymerization by the batch or metering process. Depending on the required profile of properties of the dispersion (for example particle size range, cationic activity), they can either be initially introduced in total into the aqueous liquor or initially introduced only in portions, the remainder in the latter case then being metered in alongside the monomer addition, so that their total concentration, based on the total amount of monomer, is 0.1 to 20% by weight, preferably 0.1 to 10% by weight and in particular 0.1 to 3% by weight. In addition, minor amounts of other cationic surfactants, and if appropriate also nonionic and/or amphoteric emulsifiers can moreover also be used. Cationic comonomers are not used at the same time if cationically surfactant biocidal compounds, preferably compounds of the formula (I) and/or (II), are used as emulsifiers.

A preferred embodiment of the invention comprises a system in which the biocidal cationic dispersions of polymers contain disperse polymers, the macromolecules of which contain copolymerized monomer units (calculated in % by weight, based on the polymer) of the following groups of monomers:

a) 80-99% by weight of ethylenically unsaturated monomers from the group comprising vinyl esters, (meth)acrylic esters, vinylaromatics, vinyl chloride, ethylene, (meth)acrylonitrile and diesters of maleic acid and/or fumaric acid, and b) 1-20% by weight of ethylenically unsaturated hydrophilic monomers with one or more functional groups, such as —OH, —COOH or $-CONR^1R^2$, in which $R^1$ and $R^2$ can be identical or different and stand for H or $-CH_2OR$, where R=H or $(C_1-C_8)$-alkyl.

2. The biocidal cationically surfactant compounds, preferably compounds of the formula (I) and/or (II), are subsequently added to an already prepared cationic dispersion of a polymer with up to a total content of 0.1 to 20% by weight, preferably 0.1 to 10% by weight, and in particular 0.1 to 3% by weight, based on the solids content of the dispersion. The compounds of the formula (I) and/or (II), which are usually in the form of concentrated aqueous solutions, but if appropriate also in solvents containing hydroxyl groups, are preferably diluted with water before being incorporated into the aqueous dispersion, in order to facilitate their incorporation. The cationic activity of the starting dispersion used can thereby be caused by the following factors, that is to say:

a) The presence of cationic emulsifiers and/or cationic protective colloids which have been used in the emulsion polymerization and preferably contain amino groups and/or ammonium groups as cationic charge carriers. Cationically surfactant biocidal compounds, preferably compounds of the formula (I) and/or (II), can additionally also already be used in an amount of preferably 0.1 to 10% by weight, based on the total amount of monomers, as an emulsifier in the emulsion polymerization, the biocidal properties of these compounds essentially being retained in the resulting dispersion.

Customary cationic emulsifiers which are used are, for example: higher primary, secondary and tertiary fatty amines and/or salts thereof, fatty amine oxyethylates, quaternary ammonium salts of fatty amine oxyethylates or tertiary alkylamines and quaternary alkylammonium compounds based on fatty amines.

The customary cationic protective colloids which are used, if appropriate, are, for example: polymers with amino or ammonium groups, such as, for example, cationic polyvinyl alcohol, cationic polysaccharides (for example cationic starch or Chitosan) and cationic polyelectrolytes (for example poly-diallyldimethylammonium chloride). These emulsifiers and protective colloids used as dispersion stabilizers can be employed individually or in combination, but the proportion of cationic emulsifiers should always predominate for the purpose of achieving the required fineness of the dispersion. Nonionic and/or amphoteric surfactant compounds can additionally also be used in the emulsion polymerization. The cationic starting dispersions can preferably contain, if appropriate, for example, 0 to 2.5% by weight of cationic protective colloids, 0.1 to 5% by weight of cationic emulsifier and 0 to 2% by weight of other surfactant compounds, in each case based on the polymer content in the dispersion.

b) The presence of cationic comonomer units in disperse polymers such as are usually obtained in emulsion copolymerization also using cationic comonomers. Suitable cationic comonomers are preferably α,β-ethylenically unsaturated compounds which can undergo copolymerization and contain primary, secondary or tertiary amino groups, such as, for example, dimethylaminoethyl methacrylate, dimethylaminoneopentyl acrylate, dimethylaminopropyl methacrylate, tert-butylaminoethyl methacrylate and the like, or organic or inorganic salts thereof, and/or alkylammonium compounds, such as, for example, trimethylammonium-ethyl methacrylate chloride, β-acetamidodiethylaminoethyl acrylate chloride, methacrylamidopropyltrimethylammonium chloride, diallyl-dimethylammonium chloride and the like. In general preferably 0.1 to 20% by weight, in particular 0.1 to 10% by weight, based on the total amount of monomers, of cationic comonomers is sufficient to stabilize the dispersion, and the content of quaternized compounds in the comonomers should predominate if emulsifiers and/or protective colloids are to be dispensed with in the preparation of the dispersions. However, in order to obtain the technologically advantageous fine-particled dispersions, nonionic emulsifiers and, if appropriate, protective colloids, and in particular in a concentration of preferably 0.01 to 10% by weight of emulsifier, in particular 0.01 to 5% by weight, based on the total amount of monomer, are preferably used to prepare copolymer dispersions containing cationic monomer units by emulsion polymerization. In such cases, the cationic comonomer content with amino groups can be greater than that with quaternized compounds, and the total concentration of cationic comonomers is then preferably 0.1 to 5% by weight, based on the total amount of monomers.

A preferred embodiment of the invention comprises a system in which the biocidal cationic dispersions of polymers contain disperse polymers which have been prepared by emulsion polymerization in the absence of cationically surfactant biocidal compounds or of cationic emulsifiers, in particular biocidal compounds of the formula (I) and/or (II), and of which the macromolecules contain copolymerized monomer units (calculated in % by weight, based on the polymer) of the following groups of monomers:

a) 80–99% by weight of ethylenically unsaturated monomers from the group comprising vinyl esters, (meth)acrylic esters, vinylaromatics, vinyl chloride, ethylene, (meth)acrylonitrile and diesters of maleic acid and/or fumaric acid, b) 0–19.5% by weight of ethylenically unsaturated hydrophilic monomers with one or more functional groups, such as —OH, —COOH or —CONR$^1$R$^2$, in which R$^1$ and R$^2$ can be identical or different and represent H or —CH$_2$OR, where R = H or (C$_1$–C$_8$)-alkyl, and c) 0.5–20% by weight of ethylenically unsaturated monomers containing amino and/or ammonium groups, of which at least 5% contain a quaternary ammonium group.

Cationic dispersions which have been prepared, where appropriate, by emulsion polymerization with cationic comonomers additionally also using cationic emulsifiers are not according to the invention and lie outside the subject matter of the application.

The non-cationic monomer components used in the preparation, by emulsion polymerization, of the dispersions to be used according to the invention are preferably ethylenically unsaturated compounds which can undergo copolymerization, such as can also be used for the preparation of conventional dispersions of binders, such as vinyl esters of (C$_1$–C$_{18}$)-carboxylic acids, for example vinyl acetate, vinyl propionate, vinyl versatate, vinyl laurate and vinyl stearate; (meth)acrylic esters of (C$_1$–C$_8$)-alcohols, for example methyl methacrylate, butyl methacrylate, octyl methacrylate, ethyl acrylate, isobutyl acrylate or 2-ethylhexyl acrylate; vinylaromatics, such as styrene or vinyltoluene; vinyl chloride, ethylene, (meth)acrylonitrile and diesters of maleic acid and/or fumaric acid. The monomers can be used either individually or as a mixture. Those monomers which lead to disperse polymers which are resistant to hydrolysis and are stable are preferably used. The monomers and their mixing ratios are usually chosen according to the desired technological properties of the dispersion, and the customary selection criteria known to the expert can be used to establish these. In particular, the minimum film-forming temperature (MFT) of the dispersions of polymers should be below the range or at most within the range of the envisaged application temperatures, that is to say preferably between 0° and 80° C., in particular between 0° and 40° C. If polymers with a harder formulation are used, film-forming auxiliaries or external plasticizers can be used to achieve the required MFT. If such additives are not desirable, the MFT of the cationic dispersion should preferably be in the range from 0° to 25° C. The following monomer combinations are suitable, in combination with cationic monomers or in combination with cationic emulsifiers and, if appropriate, protective colloids, for example especially preferably in the weight ratios shown below (PW=parts by weight), for the preparation of aqueous cationic dispersions in the context of the invention:

butyl acrylate/methyl methacrylate: 10-90 PW/90-10 PW butyl acrylate/styrene: 10-90 PW/90-10 PW octyl acrylate/methyl methacrylate: 5-80 PW/95-20 PW octyl acrylate/styrene; 5-80 PW/95-20 PW vinyl acetate/butyl acrylate: 40-80 PW/60-20 PW vinyl acetate/vinyl versatate: 50-80 PW/50-20 PW As regards the pattern of properties of the cationic dispersions of polymers which are to be used according to the invention, it may in some cases be advantageous also to use other comonomers in the emulsion copolymerization, and in particular, for example, ethylenically unsaturated hydrophilic compounds with one or more functional groups, such as —OH, —COOH or —CONR$^1$R$^2$, in which R$^1$ and R$^2$ can be identical or different and represent H or —CH$_2$OR, where R=H or (C$_1$-C$_8$)-alkyl. If appropriate, comonomers of this type are used in amounts of preferably 1 to 20% by weight, in particular 1 to 5% by weight, based on the total amount of monomers.

Preferred compounds from this group are, for example, hydroxyethyl methacrylate, hydroxypropyl methacrylate, polyhydroxypropyl methacrylate, hydroxyethyl acrylate, hydroxypropyl acrylate, polyhydroxypropyl acrylate, methacrylic acid, acrylic acid, maleic acid, fumaric acid, itaconic acid and the half-esters of the last three compounds mentioned, methacrylamide, acrylamide, N-methylolmethacrylamide, N-methylolacrylamide and vinylpyrrolidone.

When using unsaturated carboxylic acids, it is important that their content does not exceed 5% by weight and is preferably in the range between 0 and 2% by weight, based on the total amount of all monomers. Moreover, the Zeta potential of the resulting dispersion should under no circumstances fall into the negative range.

To establish the required fineness of the dispersion (average particle size preferably 0.02 to 0.5 μm, particularly preferably 0.05 to 0.2 μm and in particular 0.08 to 0.15 μm), cationic and/or nonionic and/or amphoteric surfactant emulsifiers are preferably used in an amount of 0.1 to 20% by weight, preferably 0.1 to 10% by weight and in particular 1 to 5% by weight, based on the total amount of monomers, in the emulsion polymerization in the customary manner. It has been found that the amounts of these emulsifiers required according to the invention in the cationic dispersions surprisingly do not have an adverse influence on the water-resistance of coatings, treatments, primer coatings and impregnations.

Emulsifiers which are used are preferably the customary nonionic surfactants, for example from the group comprising reaction products of aliphatic, cycloaliphatic, araliphatic, aliphatic-aromatic or aromatic carboxylic acids, alcohols, phenols and amines with epoxides, such as, for example, ethylene oxide, and block copolymers of various epoxides, such as, for example, ethylene oxide and propylene oxide. Other preferred emulsifiers are, for example, primary, secondary and tertiary fatty amines in combination with organic or inorganic acids and also surfactant quaternary alkylammonium compounds. Amphoteric surfactants with a Zwitter-ion structure, for example of the betaine type, such as, for example, alkylamidopropyl betaines, can moreover also be advantageous in some cases. The emulsifiers mentioned can be used in the customary manner either individually or as combinations amongst themselves or with one another. A limited amount of anionic emulsifiers can also be present in the emulsion polymerization. Preferably, however, no anionic emulsifiers are used. If they are used, however, their content should, if appropriate, be merely such that the stability of the dispersion suffers no interference, and the particles of the dispersion should not be converted in charge to a negative Zeta potential.

If appropriate, known protective colloids can additionally also be used in the preparation of the cationic dispersions, and in particular preferably those based on high molecular weight organic compounds which are water-soluble or water-dispersible and thereby essentially display no pronounced surface-active characteristics, if any, and have a pronounced dispersion capacity. Preferred protective colloids are those of a nonionic or cationic structure, such as, for example, cellulose ethers, polyvinyl alcohols, polysaccharides and polyvinylpyrrolidones, it being possible for these compounds preferably to be substituted by amino groups or quaternary ammonium groups. The latter groups can be introduced into the underlying macromolecules, for example, by substitution by means of cationization reagents, such as, for example, glycidyltrimethylammonium chloride. Cationic polyvinyl alcohols can also be obtained, for example, by hydrolysis of corresponding vinyl acetate copolymers containing amino and/or ammonium groups. The amounts of protective colloids to be used depend on the desired properties of the dispersion, in particular the fineness of the particles of the dispersion. Larger amounts of protective colloid in general act against the desired fineness of the dispersion. If appropriate, amounts of protective colloid of between 0 and 5% by weight, in particular between 0.1 and 2% by weight, if any, based on the total amounts of monomers are therefore preferably used in the emulsion polymerization.

All the systems which are customary in emulsion polymerization, preferably water-soluble systems, and which initiate free-radical chains, it also being possible for the systems to be anionic in nature, can be used to initiate the polymerization or copolymerization. Preferred initiators are, for example, 2,2'-azobis(2-amidinopropane) dihydrochloride, 2,2'-azobis-(N,N'-dimethyleneisobutyramidine) dihydrochloride, 4,4'-azobis-(4-cyanovaleric acid), H$_2$O$_2$, t-butyl hydroperoxide, persulfates, such as ammonium persulfate, sodium persulfate and potassium persulfate, redox systems, such as H$_2$O$_2$ and ascorbic acid, peroxides and polyvalent metal salts, t-butyl hydroperoxide and Rongalit, redox systems possibly being advantageous, above all, for reducing the residual monomer content in the post-reaction phase of the polymerization, and furthermore high-energy radiation and customary photoinitiators.

Customary regulators can also be used for controlling the molecular weight in the emulsion polymerization, such as, for example, mercaptans or halogenohydrocarbons for reducing the molecular weight, or if appropriate, up to 5% by weight, based on the total amount of monomers, of ethylenically polyunsaturated or polyfunctional compounds capable of crosslinking, such as, for example, divinylbenzene, ethylene glycol dimethacrylate, ethylene glycol diacrylate, butanediol dimethacrylate, butanediol diacrylate, triallyl cyanurate, melamine and isocyanatoethyl methacrylate, for increasing the molecular weight.

For the use according to the invention as biocidal treatment agents or binders or priming agents or impregnating agents, the aqueous cationic fine-particled dispersions of polymers are first brought to the content according to the invention of biocidal cationically surfactant compounds, preferably compounds of the formula (I) and/or (II), in general by mixing in aqueous dilutions of these biocidal compounds, if these have not already been used in the amount required for the biocidal activity according to the invention as an emulsifier in the emulsion polymerization, and the solids content of the dispersions is preferably brought to values of 3 to 40% by weight, in particular 5 to 20% by weight, based on the dispersion. In these preferred solids concentration ranges, the biocidal cationic dispersions have a low viscosity and a high penetrating power into porous substrates, as well as a good film-forming capacity and a good adhesive bonding capacity; they develop virtually no troublesome foam and can therefore be processed very advantageously. The dispersions have a very high stability, also in respect of the constancy of their particle size distribution.

The cationic activity of the cationic dispersions in general increases as the content of cationically surfactant compounds increases. The cationic activity can be measured, for example, titrimetrically in a known manner (cf. W. Schempp and H. T. Trau, Wochenblatt für Papierfabrikation 19, 1981, pages 726-732, or J. P. Fischer and K. Löhr, Organic Coatings Science Technology, Volume 8, pages 227-249, Marcel Dekker, Inc. April 1986).

The cationic starting dispersions in general have a cationic activity of between 1.5 and 600 $\mu$mol per g of solid, preferably between 1.5 and 150 $\mu$mol/g of solid. After addition of the biocidal cationically surfactant constituents, preferably compounds of the formula (I) and/or (II), it being possible for the addition to take place either already in the form of an emulsifier in the emulsion polymerization and/or subsequently by mixing into the finished cationic dispersion in amounts according to the invention, the biocidal cationic dispersions to be used according to the invention in general have a, total cationic activity in the range from 1.5 to 600 $\mu$mol/g of solid, preferably 10 to 300 $\mu$mol/g of solid. 5 to 95% of the total cationic activity of biocidal cationic dispersions according to the invention preferably accounts for biocidal cationic compounds, preferably compounds of the formula (I) and/or (II). It has furthermore been found that comparable amounts of biocidal compounds of the formula (I) and/or (II) in the biocidal cationic dispersions according to the invention can display a more potent and more effective biocidal activity if they have subsequently been admixed to a finished cationic dispersion instead of already being incorporated into the dispersion as an emulsifier during the emulsion polymerization. In addition to the level of the cationic activity content resulting from the cationic biocide, for example of the formula (I) or (II), amongst other things the particular specific biocidal action spectrum of the individual compounds of the formula (I) and/or (II) used or the amount of such compounds in mixtures of biocidal cationically surfactant active compounds is additionally also essential for the biocidal activity of the cationic dispersions according to the invention.

As is known, various biocides, for example of the formula (I) or (II), can, for example, have a more potent fungicidal or more potent algicidal or more potent bactericidal action than other biocidal compounds of the formula (I) or (II).

In those biocidal cationic dispersions according to the invention which are preferably used for the preparation of fungicidal and algicidal coatings or primer coatings or plasters, the total cationic activity can preferably be in the range from 10 to 75 $\mu$mol/g of solid, and 50 to 95% of this total cationic activity should preferably originate from compounds of the formula (I) and/or (II).

In those biocidal cationic dispersions for which the starting dispersions have been prepared by emulsion polymerization in the absence of biocidal cationic emulsifiers, in particular those of the formula (I) and/or (II), the latter then subsequently being admixed to the finished cationic starting dispersion, the total cationic activity of the dispersion according to the invention can preferably be 5 to 300 $\mu$mol/g of solid, in particular 15 to 150 $\mu$mol/g of solid, above the cationic activity value of the cationic starting dispersion.

In the biocidal cationic dispersions which can be used according to the invention, all the essential advantageous properties such as are known of cationic dispersions of polymers are retained, for example their ease of preparation and problem-free handling, their non-combustibility, non-toxicity and non-polluting properties. The biocidal activity of the compounds of the formula (I) and/or (II) is virtually unimpaired by the presence of the constituents of the disperse polymer and the latter, amongst other things because of their good compatibility with the biocidal active compounds, more over reduce their leachability and thereby prolong the duration of action. Since the biocidal aqueous dispersions according to the invention preferably contain no further solvents, they are also particularly suitable for applications in inside rooms because of their toxicological acceptability and their substantial odor neutrality.

The invention is illustrated in more detail by the following examples.

EXAMPLE 1

1,179.7 g of demineralized water (E water), 4.88 g of laurylpyridinium chloride (LPC) (=0.7% by weight, based on the total amount of monomers) and 10% of a mixture of 439.8 g of butyl acrylate (BA), 243.8 g of methyl methacrylate (MMA) and 9.75 g of hydroxyethyl methacrylate (HEMA) are initially introduced into a 2 l stirred reactor and heated to 80° C. After addition of 1.95 g of 4,4'-azo-bis-(4-cyanovaleric acid) (AVA) as an initiator, preliminary polymerization is carried out for 15 minutes. The remainder of the monomer mixture is then metered in over a period of 2 hours. After addition of 0.49 g of AVA, the mixture is allowed to after-react at 80° C. for 1 hour and the dispersion is cooled to room temperature. A fine-particled cationic dispersion which is biocidal according to the invention and has a cationic activity of 12 $\mu$mol/g of solid (S), measured at pH 7, an average particle diameter of 0.268 $\mu$m and an S content of 29.5% by weight is obtained. The pH of the dispersion is 3.1.

EXAMPLE 2

Example 1 is repeated, with the modification that 9.75 g of methacrylamidopropyltrimethylammonium chloride (MAPTAC) are additionally added to the initial mixture and in that instead of 4.88 g of LPC, 4.88 g of iso-tridecyl alcohol polyglycol ether (with 15 ethylene oxide units (=15 EO)) are used as the emulsifier. A fine-particled cationic dispersion with an average particle diameter of 0.186 $\mu$m, a cationic activity of 8 $\mu$mol/g of S, measured at pH 7, and an S content of 29.3% by weight is obtained. 1% by weight, based on the S content of the dispersion, of stearyldimethylbenzylammonium chloride (SDMBAC) is then added to the cationic starting dispersion thus obtained and is mixed in thoroughly, after which the resulting cationic dispersion which is biocidal according to the invention has a cationic activity of 31 $\mu$mol/g of S, measured at pH 7. The pH of the dispersion is 3.2.

EXAMPLE 3

Example 1 is repeated with the modification that instead of 4.88 g of LPC, 4.88 g of stearyldimethylbenzylammonium chloride (SDMBAC) are used as the emulsifier. The physico-chemical characteristics of the resulting dispersion which is biocidal according to the invention are essentially identical to those of Example 1. The pH of the dispersion is 3.2. The cationic activity is 17 $\mu$mol/g of S.

EXAMPLE 4

Example 1 is repeated with the modification that instead of 4.88 g of LPC, 4.88 g of didecyldimethylammonium chloride (DDDMAC) are used as the emulsifier. The physico-chemical characteristics of the resulting dispersion which is biocidal according to the invention are essentially identical to those of Example 1. The cationic activity is 35 $\mu$mol/g of S. The pH of the dispersion is 3.1.

EXAMPLE 5

Example 2 is repeated with the modification that instead of 1% by weight of SDMBAC, 1% by weight, based on the S content of the dispersion, of didecyldimethylammonium chloride (DDDMAC) is added to the cationic starting dispersion obtained and is mixed in thoroughly. The physico-chemical characteristics of the resulting dispersion, which is biocidal according to the invention, are essentially identical to those of Example 2. The pH of the dispersion is 3.1. The cationic activity is 36 $\mu$mol/g of S.

EXAMPLE 6

Example 2 is repeated with the modification that instead of 1% by weight of SDMBAC, 1% by weight, based on the S content of the dispersion, of laurylpyridinium chloride (LPC) are added to the cationic starting dispersion obtained and are mixed in thoroughly. The physico-chemical characteristics of the resulting dispersion, which is biocidal according to the invention, are essentially identical to those of Example 2. The cationic activity is 22 $\mu$mol/g of S. The pH of the dispersion is 3.1.

COMPARISON EXAMPLE 1

For comparison, a customary anionic fine-particled dispersion of a polymer, prepared in accordance with DE-PS 2,531,895, Example 1, with 34.6% by weight of S, an average particle diameter of 0.047 $\mu$m and without a content of cationic biocidal active compound is used for the comparative tests described below. The dispersion is brought to pH 8 with aqueous ammonia.

APPLICATION TESTS

The dispersions according to the invention can be evaluated for their biocidal activity by a procedure in which samples of dried customary facade plaster based on a dispersion of a polymer and samples of dried customary paints based on a dispersion of a polymer are subjected to comparative priming with in each case one of the biocidal dispersions of Examples 1 to 6 according to the invention or, for comparison, with the dispersion of Comparison Example 1 which is not according to the invention, and after drying the samples are placed on microbially infected agaragar nutrient media and the biocidal activity, in particular against fungi and algae, is observed. In detail, the procedure here can be as follows.

Filter-paper circles of 5.5 cm diameter are coated with an approximately 3 mm thick layer of a facade plaster formulation (scraped rendering) which has been prepared in accordance with facade plaster recipe 1 shown below, without also using preservatives, and the coated test specimens are dried in air at room temperature for 14 days.

In an analogous manner to the preparation of facade plaster test speciments, filter-paper circles 5.5 cm in diameter are coated with an approximately 0.3 mm thick layer of an emulsion paint which has been prepared in accordance with emulsion paint recipe 1 given below, without also using preservatives, and the coated test specimens are dried in air at room temperature for 14 days.

The dried facade plaster and paint film test specimens are then primed by wet application of a biocidal dispersion of Examples 1 to 6 according to the invention, diluted 1:1 with water, or the dispersion of Comparison Example 1 which is not according to the invention, and the primed test specimens are dried again in air at room temperature for 14 days. The biological inhibition tests described below are carried out on correspondingly microbially infected agar-agar nutrient media with the test specimens dried and treated in this way.

| Facade plaster recipe 1 White facade plaster* (scraped rendering) based on a dispersion of a polymer, for external and internal use | |
|---|---|
| Constituents | Parts by weight |
| Aqueous copolymer dispersion based on vinyl acetate/vinyl Versatate 70/30, 50% by weight solids content | 180.0 |
| Concentrated ammonia (25% strength by weight, aqueous) | 0.5 |
| 2% strength by weight aqueous solution of methylhydroxyethylcellulose (Tylose MH 6000 K) | 30.0 |
| 10% strength by weight aqueous polyphosphate solution (Calgon N) | 2.0 |

-continued

Facade plaster recipe 1
White facade plaster* (scraped rendering) based on a
dispersion of a polymer, for external and internal use

| Constituents | Parts by weight |
|---|---|
| Antifoam (Nopco 8034) | 2.0 |
| Titanium dioxide powder (Kronos RNCX) | 45.0 |
| Calcium carbonate, consisting of | |
| Omya Durcal, 40 μm particle size | 150.0 |
| Omya Durcal, 130 μm particle size | 170.0 |
| Omya Granicalcium, 0.35-0.7 mm particle size | 100.0 |
| Omya Granicalcium, 1-2 mm particle size | 300.0 |
| White spirit | 12.5 |
| Butyldiglycol acetate | 3.0 |
| Dibutyl phthalate | 3.0 |

*The constituents of the recipe are uniformly mixed in the customary sequence to give a ready-to-use facade plaster formulation and are applied directly to filter-paper circles to prepare the test specimens required.

Emulsion paint recipe 1
Aqueous emulsion paint* for external and internal use

| Constituents | Parts by weight |
|---|---|
| Aqueous copolymer dispersion based on vinyl acetate/vinyl Versatate 70/30, 50% by weight solids content | 340.0 |
| Concentrated ammonia (25% strength by weight, aqueous) | 1.0 |
| 2% strength by weight aqueous solution of methylhydroxyethylcellulose (Tylose MH 2000 K) | 85.0 |
| 10% strength by weight aqueous polyphosphate solution (Calgon N) | 7.0 |
| Antifoam (Nopco 8034) | 3.5 |
| Titanium dioxide powder (Kronos RNCX) | 135.0 |
| Calcium carbonate, consisting of | |
| Omya Durcal, 5 μm particle size | 114.0 |
| Omya Calibrite SL | 170.0 |
| Aluminum silicate (China clay B) | 40.0 |
| Magnesium silicate (Micro-Talc A.T.1) | 17.0 |
| Water | 63.0 |
| White spirit | 12.0 |
| Butyldiglycol acetate | 5.0 |
| Dibutyl phthalate | 5.0 |

*The constituents of the recipe are uniformly mixed in the customary sequence to give a ready-to-use emulsion paint and are applied directly to filter-paper circles to prepare the test specimens required.

BIOLOGICAL INHIBITION TEST

The primed and dried test specimens described above are rendered germ-free by means of UV light and placed on agar-agar nutrient media which have been inoculated with fungi (Aspergillus niger) or with algae (Chlorella pyrenoidosa), in Petri dishes.

The samples inoculated with fungi are placed in an incubating cabinet at 29° C. and 70% relative atmospheric humidity for 8 days and the fungal growth is subsequently evaluated in accordance with the following scale of ratings from 1 to 4:
  1 = no growth on test specimen; no inhibition zone in the agar-agar
  2 = slight growth on test specimen (less than 10%)
  3 = clear growth on test specimen (less than 30%)
  4 = severe growth on test specimen (more than 30%).

The samples inoculated with algae are left to stand on a laboratory bench under artificial light at room temperature (20° C.) (to activate the photosynthesis) for 14 days and the algal growth is then evaluated in accordance with the following scale of ratings from 0 to 4:
  0 = no growth on test specimen
  1 = slight growth on test specimen
  2 = clear growth on test specimen
  3 = severe growth on test specimen
  4 = very severe growth on test specimen.

In a further test, the primed and dried test specimens described above are first kept in running water for 24 hours and then dried again, rendered germ-free by means of UV light and placed on agar-agar nutrient media which have been inoculated with fungi (Aspergillus niger) or with algae (Chorella pyrenoidosa), in Petri dishes. Incubation and subsequent evaluation of the samples in the Petri dishes is carried out in a manner analogous to that described above for the samples which have not been kept in water.

The results are summarized in Table 1. It is particularly remarkable here that the samples which have been preserved according to the invention lose virtually none of their fungus-inhibiting action by being kept in water, and in addition show an unexpectedly good inhibiting behavior in comparison with samples which have been primed with customary dispersions in accordance with Comparison Example 1.

TABLE 1

Biological inhibition test on facade plaster and emulsion paint test specimens preserved according to the invention.

| Facade plaster test specimen (F) or emulsion paint test specimen (E), primed with a dispersion from Example No. 1 to 6 or Comparison Example 1 | Evaluation of the infected and incubated samples (Fungi: 1 = no growth, 4 = severe growth; Algae: 0 = no growth, 4 = severe growth) (a) Test specimens not kept in water (b) Test specimens kept in water | | | |
|---|---|---|---|---|
| | Fungi | | Algae | |
| | (a) | (b) | (a) | (b) |
| Example 1 (F) | 2 | 1 | 0 | 0 |
| Example 1 (E) | 2 | 1 | 0 | 0 |
| Example 2 (F) | | | 0 | 3 |
| Example 2 (E) | | | 0 | 3 |
| Example 3 (F) | 1 | 1 | 0 | 3 |
| Example 3 (E) | 1 | 1 | 0 | 3 |
| Example 4 (F) | 1 | 1 | 0 | 2 |
| Example 4 (E) | 1 | 1 | 0 | 2 |
| Example 5 (F) | | | 0 | 1 |
| Example 5 (E) | | | 0 | 1 |
| Example 6 (F) | 3 | 4 | 0 | 2 |
| Example 6 (E) | 3 | 4 | 0 | 2 |
| Comparison Example 1 (F) | 4 | 4 | 0 | 4 |
| Comparison Example 1 (E) | 4 | 4 | 0 | 4 |

We claim:

1. An antimicrobial composition comprising an antimicrobically effective amount of a fine particle dispersion containing a biocidally, cationcally active surfactant quaternary ammonium compound in an aqueous media, wherein the dispersion of a cationic polymer contains biocidal cationically surfactant quaternary organic ammonium compounds of the formula I and/or II

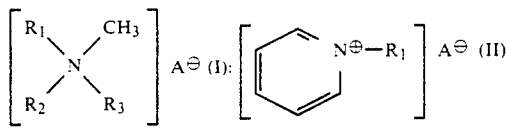

in which
$R_1 = (C_8-C_{18})$-alkyl or -alkenyl,
$R_2 = (C_8-C_{18})$-alkyl or -alkenyl, aryl or $(C_7-C_{18})$-aralkyl, in which the aromatic rings are unsubstituted or substituted with at least one member of the group consisting of chlorine and bromine
$R_3 = (C_1-C_4)$-alkyl or the radical $-(CH_2-CHR^4O)-_n-R^5$, in which n denotes a number from 1 to 20 and $R^4$ and $R^5$, which can be identical or different, denote H and/or $(C_1-C_4)$-alkyl, and
A = an anion of an organic or inorganic acid.

2. A composition of claim 1 wherein $R_3$ is methyl.

3. A composition as claimed in claim 1, wherein the biocidal cationic dispersion of a polymer contains 0.1 to 20% by weight, based on the disperse polymer, of at least biocidal cationically surfactant quaternary organic ammonium compounds.

4. A composition as claimed in claim 1, wherein the average particle diameter of the disperse polymer in the dispersion is 0.02 to 0.5 μm.

5. A composition as claimed in claim 1, wherein the solids content of the biocidal cationic dispersion of a polymer is 3 to 40% by weight, based on the dispersion.

6. A composition as claimed in claim 1, wherein the biocidal cationic dispersion of a polymer has a cationic activity of 1.5 to 600 μmol/g of solid, measured at pH 7.

7. A composition as claimed in claim 1, wherein 5 to 95% of the total cationic activity accounts for a biocidal cationically surfactant quaternary organic ammonium compound.

8. A composition as claimed in claim 1 wherein the biocidal cationic dispersion of a polymer contains disperse polymers, the macromolecules of which contain copolymerized monomer units (calculated in % by weight, based on the polymer) of the following groups of monomers:
a) 80-99% by weight of ethylenically unsaturated monomers from the group comprising vinyl esters, (meth)acrylic esters, vinylaromatics, vinyl chloride, ethylene, (meth)acrylonitrile and diesters of maleic acid and/or fumaric acid, and
b) 1-20% by weight of ethylenically unsaturated hydrophilic monomers with one or more functional groups.

9. A composition of claim 8 wherein the functional groups of the b) component are selected from the group consisting of —OH, —COOH and

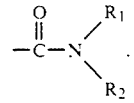

$R_1$ and $R_2$ are individually hydrogen or —CH$_2$OR and R is hydrogen or alkyl of 1 to 8 carbon atoms.

10. A process for biocidal treatment of a substrate susceptible to attack from microbes from microbes wherein the substrate is treated fungicidally, bactericidally and/or algicidally with a composition of claim 1.

* * * * *

UNITED STATES PATENT AND TRADEMARK OFFICE
CERTIFICATE OF CORRECTION

PATENT NO. : 5,049,383
DATED : Sept. 17, 1991
INVENTOR(S) : Hans-Ullrich Huth, Helmut Braum and Franz Konig It is certified that error appears in the above-identified patent and that said Letters Patent is hereby corrected as shown below:

Col.    Line

15    Claim 1, Lines 25 & 26

"$-(CH_2-CHR^4O)-_n-R^5$"

should be -- $-(CH_2-CHR^4O)_n-R^5$ --

Signed and Sealed this

Twenty-third Day of February, 1993

*Attest:*

STEPHEN G. KUNIN

*Attesting Officer*    *Acting Commissioner of Patents and Trademarks*